United States Patent [19]

Fellman

[11] Patent Number: 5,017,471
[45] Date of Patent: May 21, 1991

[54] REAGENT FOR PEROXIDASE DETECTION

[75] Inventor: Jack H. Fellman, Portland, Oreg.

[73] Assignee: Epitope, Inc., Beaverton, Oreg.

[21] Appl. No.: 236,896

[22] Filed: Aug. 26, 1988

[51] Int. Cl.$^5$ .......................... C12Q 1/70; C12Q 1/28; G01N 33/544; G01N 33/53

[52] U.S. Cl. .......................................... 435/5; 435/28; 435/7.92; 435/7.95; 435/974; 436/530; 436/547; 436/161; 436/164

[58] Field of Search ...................... 435/5, 28, 810, 802, 435/530, 7; 436/547, 111, 161, 164, 66, 135, 904, 127, 136

[56] References Cited

U.S. PATENT DOCUMENTS

| | | | |
|---|---|---|---|
| 2,905,594 | 9/1959 | Morris | 435/28 |
| 3,087,794 | 4/1963 | Free et al. | 23/253 |
| 4,013,404 | 3/1977 | Parent et al. | 8/423 |
| 4,278,439 | 7/1981 | White | 23/230 |
| 4,337,061 | 6/1982 | Bugaut et al. | 564/97 |
| 4,521,511 | 6/1985 | Stout | 435/28 |
| 4,665,023 | 5/1987 | Deneke et al. | 435/28 |
| 4,670,402 | 6/1987 | Flegler | 436/904 |
| 4,721,670 | 1/1988 | Osada et al. | 435/28 |
| 4,729,950 | 3/1988 | Kricka | 435/28 |

OTHER PUBLICATIONS

Tsang et al., "Enzyme Linked Immunotransfer Blot Techniques (EITB) for Studying the Specifities of Antigens and Antibodies Separated by Gel Electrophoresis", Methods in Enzymology, (1983), pp. 378–391.
Epitope Inc. Brochure–Epitope EPIblot–HIV Western Blot Kit, (Dec. 1987).

Primary Examiner—Esther L. Kepplinger
Assistant Examiner—Janelle Graeter
Attorney, Agent, or Firm—Eugene D. Farley

[57] ABSTRACT

A storage-stable, non carcinogenic reagent for peroxidase detection useful in the diagnosis of AIDS and other diseases which comprises an aqueous solution of hydrogen peroxide and a chromogen therefor. Chromogens uniquely suitable for the purpose are:

5 amino-indole
7 amino-indole
5 amino-benzimidazole
7 amino-benzimidazole
5 amino-benzothiazole
7 amino-benzothiazole
5 amino-benzoxazole
7 amino-benzoxazole
5 amino-indazole
7 amino-indazole 17 Claims, No Drawings

REAGENT FOR PEROXIDASE DETECTION

This invention relates to a reagent for peroxidase detection. It pertains particularly to a reagent useful in the detection in human blood plasma and serum of the antibodies for AIDS and other viruses, thereby affording a useful method of diagnosis for the virus-caused diseases.

BACKGROUND AND GENERAL STATEMENT OF THE INVENTION

One of the useful tools in immunology is the detection of antigens by enzymes linked to antibodies. This technology employs a substrate which the enzymes process in such a manner as to signal the presence of the antigen if antibodies are present which correspond to the disease for which diagnosis is sought.

A typical and particularly useful procedure of this class is the enzyme immunoassay procedure for the detection of the antibody to human immunodeficiency (AIDS) virus in human blood serum or plasma. This procedure is also known as, and is termed herein, the Western Blot procedure. (Tsang, Victor C. W., Peralta, Jose M., and Simons A. Ray, Methods in Enzymology, Vol. 92, 377–391 (1983). "[29] Enzyme-linked Immunoelectrotransfer Blot Techniques (EITB) for the Study of the Specificities of Antigens and Antibodies separated by Gel Electrophoresis"; see particularly page 377, second paragraph and pages 383–7 for descriptions of the procedure which has become known as the Western Blot procedure.).

Briefly stated, the Western blot procedure takes advantage of the fact that the AIDS and other viruses are constituted by a number of different proteins having different molecular sizes. These can be segregated according to size by subjecting the virus on gel to an applied electric field. Thereupon the proteins migrate distances determined by their molecular weight, thereby segregating them.

In applying the Western blot technique, the segregated proteins are transferred by blotting onto a piece of nitrocellulose or other specifically absorbent paper.

The paper containing the virus protein next is cut into strips and the strips exposed to human blood sera suspected of containing antibodies to the AIDS virus (e.g. "sero-positive" AIDS patients). If antibodies are present, they will adhere specifically to the corresponding viral protein. The strip is washed to remove any material not thus specifically adherent to the viral protein.

The strip mounting the combination of viral protein and antibody next is exposed to a solution containing a second antibody (e.g., goat anti-human antibody), which will bind specifically to human-derived antibodies. To the goat anti-human antibody is chemically (covalently) bound (conjugated) a peroxidase enzyme such as horseradish peroxidase.

The goat antibody thus serves as a carrier for the enzyme and binds it to the viral protein-antibody complex. If the serum under diagnosis in fact contains antibodies to the virus, there thus is formed a complex of AIDS virus protein, serum-derived antibodies to such protein, and goat anti-human antibody to which is chemically bound an enzyme peroxidase. The strip is washed with phosphate-buffered saline solution, or other suitable wash liquid, to remove other materials.

The strip now is exposed to a reagent containing buffered hydrogen peroxide and a chromogen. If the strip contains the enzyme peroxidase, which it can contain only in the event that it also mounts AIDS antibodies, the peroxidase will act with the hydrogen peroxide co-substrate, to peroxidize the chromogen co-substrate, converting it to an intensely dark brown, highly visible product. The oxidized product is insoluble and deposits on the strip precisely where the electrophoretically deposited antibody proteins are located.

The result of this procedure is a blot strip having a characteristic pattern of highly colored bands, if the diagnostic test is positive. No such bands will be present on the strip if the test is negative.

The chromogen-containing reagent thus serves as an indicator for making visible the peroxidase on the strip. A number of different chromogens have been proposed for use in this procedure. A commonly employed chromogen is diamino benzidine.

The reagents of the prior art which have been applied in the Western Blot procedure have suffered from very short shelf lives. The co-substrate hydrogen peroxide which if present in the reagent together with the chromogen substrate is per se an oxidizing agent which has the inherent capacity for converting the chromogen in a short time to its colored derivative.

The chromogen substrates of the prior art also are relatively insensitive and carcinogenic.

It is the general purpose of the present invention to provide a non-carcinogenic reagent which has a shelf life of six months or more when mixed with its co-substrate hydrogen peroxide, and which, in addition, is highly sensitive to reaction, being converted rapidly to an intensely colored, highly visible, insoluble product when contacted with even very small amounts of the peroxidase component of the Western Blot test strip.

This result is achieved by inclusion in the reagent of a proportion of a unique chromogen of the general formula

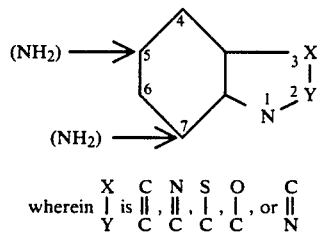

$$\text{wherein } \begin{matrix} X \\ | \\ Y \end{matrix} \text{ is } \begin{matrix} C \\ \| \\ C \end{matrix}, \begin{matrix} N \\ \| \\ C \end{matrix}, \begin{matrix} S \\ | \\ C \end{matrix}, \begin{matrix} O \\ | \\ C \end{matrix}, \text{ or } \begin{matrix} C \\ \| \\ N \end{matrix}$$

and the benzene ring is substituted at the 5 or 7 position with an amino group.

More explicitly, the chromogens useful in the reagents of the invention comprise members of the following group:

5 amino-indole
7 amino-indole
5 amino-benzimidazole
7 amino-benzimidazole
5 amino-benzothiazole
7 amino-benzothiazole
5 amino-benzoxazole
7 amino-benzoxazole
5 amino-indazole
7 amino-indazole These materials have the unique quality of stability in the presence of hydrogen peroxide so that the reagents of the invention remain stable over periods of several months, thus rendering them suitable for commercial application. They also are non-carcinogenic. Still further, they are extremely sensitive to the presence of minute quantities of peroxidase and develop in the presence of hydrogen peroxide an intense coloration of the bands of the test strip if disease antibodies are present on it.

The underlying basis for the special properties of the above group of chromogens is determined by the fact that they all comprise nitrogen compounds of which a nitrogen atom is a component of a heterocyclic ring. This imparts stability to the chromogen.

When placed in contact with the antibody-bound peroxidase in the presence of hydrogen peroxide, the chromogen first is converted to a quinimine monomer characterized by the presence of positive charges at the 4, 6 and 7 carbon atoms in the case of the 5-amino chromogens, and at the 4, 5 and 6 positions in the case of the 7-amino chromogens. This characteristic, in turn, promotes polymerization of the monomer to a highly colored random polymer linearly and cross-linked at the 4, 6 and 7 carbon atoms in the one case, and at the 4, 5 and 6 carbon atoms in the other. The resulting polymer is water insoluble because of its molecular content of a large member of hydrophobic aromatic rings.

In either case, when carrying out the Western blot test described above, the highly colored polymeric product deposits at the site of the co-valently bound enzyme, thus designating specifically the position of the bound antibody on the test strip.

DESCRIPTION OF PREFERRED EMBODIMENTS OF THE INVENTION

As noted above, the reagents of the invention are applicable in the diagnosis of various diseases by the Western Blot procedure. They are applicable in all such procedures which make use of the peroxidase enzyme as a part of the diagnostic system. They are particularly useful in the diagnosis of AIDS, but potentially useful also in the identification of the human leukemia virus and other disease-causing viruses.

They are useful further with various peroxide-peroxidase systems. The commonly employed peroxide component of such systems is, of course, hydrogen peroxide.

Peroxidases which may be employed together with the hydrogen peroxide may be derived from various sources, such as horseradish peroxidase, potato peroxidase and other plant peroxidases.

Although goat antihuman antibody may be employed to advantage as the preferred carrier for the selected peroxidase, other antihuman antibodies derived from other sources also may be employed. These include: rabbit—sheep— and horse—antihuman antibodies.

The unique chromogens which may be employed as indicators to detect the presence of the antigen by the peroxidase enzyme comprise one or more of the following group:
  5 amino-indole
  7 amino-indole
  5 amino-benzimidazole
  7 amino-benzimidazole
  5 amino-benzothiazole
  7 amino-benzothiazole
  5 amino-benzoxazole
  7 amino-benzoxazole
  5 amino-indazole
  7 amino-indazole The reagent of the invention comprises a simple mixture of the hydrogen peroxide, and the selected chromogen in aqueous medium.

Broadly stated, the amount of hydrogen peroxide employed lies within the reactive minimum amount required to react with its peroxidase co-substrate, and the maximum amount, use of which will destroy the enzyme. A preferred range of hydrogen peroxide use is from 1-30 mg peroxide per 100 ml reagent.

Broadly stated, the amount of chromogen employed is that amount which, under the conditions of the reaction, will develop a sufficient coloration to indicate a positive test when disease antibodies are present. The lower limit of chromogen use is that amount which will develop such a coloration; the upper limit, the amount which will saturate the aqueous reagent medium with chromogen, i.e. a saturated solution of chromogen. Within this broad range, the chromogen use is adjusted to provide a reagent the application of which develops optimum color characteristics in use. Typical chromogen usages lie within the range of from 0.1 mg chromogen/100 ml of reagent up to the amount required to saturate the solution with chromogen. A preferred range is from 5 mg chromogen/100 ml reagent up to the amount required to saturate the solution with chromogen.

The reagents of the invention normally are prepared and used at temperatures lying in the broad range defined by that temperature at which the reagent retains its chemical activity (lower limit) and that temperature at which the enzyme is killed (upper limit). A practical working temperature range is from 15°-30° C.

The aqueous solution of peroxide and chromogen should be buffered to a pH level at which the enzyme operates favorably. This may be accomplished by a pH adjustment with sodium hydroxide, sodium phosphate or other suitable base, to a pH level of from pH 4.0 to 8.5, preferably to a level of pH 7.0 to 7.6.

The reagents are prepared simply by dissolving the chromogen in the buffered saline using an acid such as hydrochloric acid or phosphoric acid as the agent of solution. The pH is adjusted to the desired level by the addition of sodium hydroxide or other basic material, after which the hydrogen peroxide is added and mixed in.

EXAMPLES

Example 1

This example illustrates the process of the invention as applied to a reagent including hydrogen peroxide and 5 amino-indole as the chromogen.

Eight liters of phosphate buffered saline were measured into a 20 liter plastic container. 10 Grams of 5 amino-indole were added and mixed with stirring for approximately 5 minutes.

The resulting reagent was adjusted to pH 2 using concentrated hydrochloric acid. This required about 20 mls. of hydrochloric acid.

Stirring was continued until the 5 amino-indole was fully dissolved. This required about 1 hour.

Thereafter the pH of the reagent was adjusted to a level of 7.2 using 2M sodium hydroxide. From 100-120 mls. of 2M sodium hydroxide was needed.

2 g of "Thimerosal" preservative and 2 ml. 30% hydrogen peroxide were added. The mixing was continued for 15 more minutes.

The volume was brought up to 20 liters by the addition of phosphate buffered saline. The resulting reagent was stored at 4° C. in the dark. Thereafter it was allowed to stand for 14 days and filtered using a 5 micron filter. When stored at 4° C. in the dark it was stable for 6 months. It then was used as the chromogen reagent in the identification of the AIDS virus by the Western Blot technique, which was carried out as follows:

Purified, inactivated AIDS virus was electrophoretically resolved into bands and transblotted onto nitrocellulose sheets. The sheets were cut into strips.

Patient serum samples to be tested were diluted in phosphate buffered saline and added to each preblotted nitrocellulose strip. If antibodies to specific human immunovirus proteins were present, these would bind to epitopes contained in the proteins banded on the strip. Any antibodies not bound were removed by washing with water.

Horseradish peroxidase and goat anti-human immunoglobulin were combined to form a conjugate peroxidase-labeled anti-human immunoglobulin. The resulting conjugate was added to the strip and allowed to incubate. Incubation was performed by permitting the sample to stand for 1 hour at room temperature with rotation or, in the alternative, 16-24 hours at 40° C. with no rotation.

During this time the conjugate bonded to any human antibodies, which already were bound to viral protein on the strip. Excess conjugate was removed by washing with water.

Next the hydrogen peroxide-chromogen reagent was added to the strip. In the case of a positive test for AIDS, dark brown bands were made visible immediately wherever the peroxidase-labeled antibody was bound.

Example 2

In a manner similar to the foregoing, reagents of the invention are formulated using in place of the 5-amino-indole of Example 1 the following chromogens:

7 amino-indole
5 amino-benzimidazole
7 amino-benzimidazole
5 amino-benzothiazole
7 amino-benzothiazole
5 amino-benzoxazole
7 amino-benzoxazole
5 amino-indazole
7 amino-indazole

Example 3

This example illustrates the stability in storage and sensitivity of the herein described reagent.

In a manner similar to that set forth in Example 1, a conventional reagent was prepared using diaminobenzidine as the chromogen. After mixing with the co-substrate, hydrogen peroxide, the mixture was observed to oxidize spontaneously at room temperature. At the end of 12 hours almost complete degradation of the chromogen had occurred and the mixture could no longer be used for peroxidase detection.

By way of contrast, the reagent of Example 1 was stable, and effective in use for peroxidase detection after a room temperature storage period in excess of six (6) months.

Having thus described in detail preferred embodiments of the present invention, it will be apparent to those skilled in the art that various changes can be made in the composition described herein without altering the inventive concepts and principles embodied. The present embodiments are therefore to be considered in all respects as illustrative and not restrictive, the scope of the invention being indicated by the appended claims.

I claim:

1. In the Western Blot procedure for enzyme immunoassay for the detection of antibodies present in human blood serum or plasma and comprising the sequential steps of
   (1) electroblotting a viral antigen onto a test piece of absorbent material,
   (2) applying to the test piece a blood serum or plasma sample suspected of containing antibodies to the viral antigen, followed by washing,
   (3) contacting the test piece with a conjugate of anti-human antibody and a peroxidase enzyme, and washing,
   (4) exposing the test piece to a reagent comprising a peroxide and a chromogen, and thereafter,
   (5) determining the appearance or absence of color in the test piece,
   the improvement which comprises:
   exposing the test piece in step (4) to a reagent comprising an aqueous solution of a peroxide and a chromogen containing at least one member selected from the group consisting of
   5 amino-indole,
   7 amino-indole,
   5 amino-benzimidazole,
   7 amino-benzimidazole,
   5 amino-benzothiazole,
   7 amino-benzothiazole,
   5 amino-benzoxazole,
   7 amino-benzoxazole,
   5 amino-indazole and
   7 amino-indazole
   the chromogen being used in amount sufficient to generate a detectable coloration of the reagent upon contacting the reagent with the peroxidase,
   the solution being buffered to a pH level predetermined to maintain the chromogen in solution.

2. The reagent of claim 1 wherein the peroxide is used in the amount of from 1 to 30 mg/100 ml of reagent.

3. The reagent of claim 1 wherein the chromogen is used in an amount of from 5 mg/100 ml of reagent up to that amount required to saturate the aqueous solution with chromogen.

4. The reagent of claim 1 wherein the peroxide is used in the amount of from 1 to 30 mg/100 ml of reagent, the chromogen is used in an amount of from 5 mg/100 ml of reagent up to that amount required to saturate the aqueous solution with chromogen, and the pH of the reagent is from pH 4 to pH 8.5.

5. The Western Blot enzyme immunoassay Procedure of claim 1 wherein the solution is buffered to a pH of from 4.0 to 8.5.

6. The Western Blot enzyme immunoassay Procedure of claim 1 wherein the chromogen comprises 5 amino-indole used in a concentration of from 5 mg/100 ml of reagent up to that amount required to saturate the aqueous solution with chromogen, the peroxide is used in a concentration of from 1 to 30 mg/100 ml of reagent, and the reagent has a pH of from 7.0 to 7.6.

7. The method of claim 1 wherein the peroxide comprises hydrogen peroxide.

8. The method of claim 1 wherein the antibodies are AIDS antibodies.

9. In the Western Blot immuno-assay procedure for the detection of virus antibodies present in human blood serum or plasma, the procedure comprising:
   (a) forming a complex of (1) a viral antigen (2) a serum or plasma sample suspected of containing an antibody to the viral antigen, and (3) a conjugate of anti-human antibody and a peroxidase enzyme, and
   (b) contacting the complex with a reagent comprising hydrogen peroxide and a chromogen and determining the development or absence of color in the resulting reagent-containing mixture, the improvement comprising:
   employing as the chromogen component of the reagent at least one member selected from the group consisting of
   5 amino-indole,
   7 amino-indole,
   5 amino-benzimidazole,
   7 amino-benzimidazole,
   5 amino-benzothiazole,
   7 amino-benzothiazole,
   5 amino-benzoxazole,
   7 amino-benzoxazole,
   5 amino-indazole, and
   7 amino-indazole.

10. The method of claim 9 wherein the chromogen is 5-amino-indole.

11. In the Western Blot procedure for enzyme immunoassay for the detection of antibodies present in human blood serum or plasma and comprising the sequential steps of
   (1) electroblotting a viral antigen onto a test piece of material,
   (2) applying to the test piece a serum or plasma sample suspected of containing antibodies to the antigen, followed by washing,
   (3) contacting the test piece with a conjugate of anti-human antibody and a peroxidase enzyme, and washing,
   (4) exposing the test piece to a reagent comprising a peroxide and a chromogen, and thereafter,
   (5) determining the appearance or absence of color in the test piece, the improvement which comprises:
   exposing the test piece in step (4) to a reagent comprising an aqueous solution of a peroxide and a chromogen of the general formula $$(NH_2) \rightarrow \underset{6}{\overset{4}{\underset{7}{\bigcirc}}} \overset{3}{\underset{1}{\overset{|}{\underset{N}{\diagdown}}}} \overset{X}{\underset{Y}{\diagup}}$$

wherein $\genfrac{}{}{0pt}{}{X}{Y}$ is $\genfrac{}{}{0pt}{}{C}{C}$, $\genfrac{}{}{0pt}{}{C}{C}$, $\genfrac{}{}{0pt}{}{N}{C}$, $\genfrac{}{}{0pt}{}{S}{C}$, $\genfrac{}{}{0pt}{}{O}{C}$, or $\genfrac{}{}{0pt}{}{C}{N}$ and the benzene ring is substituted at the 5 or 7 position with an amino group,
the chromogen being used in amount sufficient to generate a detectable coloration of the reagent upon contacting the reagent with the peroxidase enzyme,
the solution being buffered to a pH level predetermined to maintain the chromogen in solution.

12. A reagent for peroxidase detection which comprises:
   an aqueous solution of hydrogen peroxide and a chromogen comprising 5 amino-benzimidazole,
   the chromogen being used in amount sufficient to generate a detectable coloration of the reagent upon contacting the reagent with peroxidase,
   the solution being buffered to a pH level predetermined to maintain the chromogen in solution.

13. A reagent for peroxidase detection which comprises:
   an aqueous solution of hydrogen peroxide and a chromogen comprising 7 amino-benzimidazole,
   the chromogen being used in amount sufficient to generate a detectable coloration of the reagent upon contacting the reagent with a peroxidase,
   the solution being buffered to a pH level predetermined to maintain the chromogen in solution.

14. A reagent for peroxidase detection which comprises:
   an aqueous solution of hydrogen peroxide and a chromogen comprising 5 amino-benzothiazole,
   the chromogen being used in amount sufficient to generate a detectable coloration of the reagent upon contacting the reagent with a peroxidase,
   the solution being buffered to a pH level predetermined to maintain the chromogen in solution.

15. A reagent for peroxidase detection which comprises:
   an aqueous solution of hydrogen peroxide and a chromogen comprising 7 amino-benzothiazole,
   the chromogen being used in amount sufficient to generate a detectable coloration of the reagent upon contacting the reagent with a peroxidase,
   the solution being buffered to a pH level predetermined to maintain the chromogen in solution.

16. A reagent for peroxidase detection which comprises:
   an aqueous solution of hydrogen peroxide and a chromogen comprising 5 amino-benzoxazole,
   the chromogen being used in amount sufficient to generate a detectable coloration of the reagent upon contacting the reagent with a peroxidase,
   the solution being buffered to a pH level predetermined to maintain the chromogen in solution.

17. A reagent for peroxidase detection which comprises:
   an aqueous solution of hydrogen peroxide and a chromogen comprising 7 amino-benzoxazole,
   the chromogen being used in amount sufficient to generate a detectable coloration of the reagent upon contacting the reagent with a peroxidase,
   the solution being buffered to a pH level predetermined to maintain the chromogen in solution.

* * * * *